United States Patent
Guo et al.

(10) Patent No.: US 8,597,648 B2
(45) Date of Patent: Dec. 3, 2013

(54) FULLY HUMAN ANTI-TNF-ALPHA MONOCLONAL ANTIBODY, PREPARATION METHOD AND USE THEREOF

(75) Inventors: Huaizu Guo, Shanghai (CN); Chuan Li, Shanghai (CN); Xin Tong, Shanghai (CN)

(73) Assignee: Shanghai Biomabs Pharmaceuticals Co., Ltd. (CN)

( * ) Notice: Subject to any disclaimer, the term of this patent is extended or adjusted under 35 U.S.C. 154(b) by 0 days.

(21) Appl. No.: 13/579,208

(22) PCT Filed: Apr. 16, 2010

(86) PCT No.: PCT/CN2010/000512
§ 371 (c)(1),
(2), (4) Date: Aug. 15, 2012

(87) PCT Pub. No.: WO2011/103701
PCT Pub. Date: Sep. 1, 2011

(65) Prior Publication Data
US 2012/0308575 A1    Dec. 6, 2012

(30) Foreign Application Priority Data
Feb. 25, 2010   (CN) .......................... 2010 1 0125249

(51) Int. Cl.
*A61K 39/395*    (2006.01)
*C07K 16/24*    (2006.01)
*C12N 5/10*    (2006.01)
*C12N 15/13*    (2006.01)
*C12N 15/00*    (2006.01)

(52) U.S. Cl.
USPC .................. 424/145.1; 424/130.1; 424/133.1; 424/141.1; 424/158.1; 424/142.1; 435/69.6; 435/326; 435/335; 435/252.3; 435/320.1; 530/387.1; 530/387.3; 530/388.15; 530/388.23; 536/23.1; 536/23.5; 536/23.53

(58) Field of Classification Search
None
See application file for complete search history.

(56) References Cited

U.S. PATENT DOCUMENTS

2007/0081996 A1    4/2007    Abi-Saab et al.

FOREIGN PATENT DOCUMENTS

CN    1613874    5/2005

*Primary Examiner* — Phillip Gambel
(74) *Attorney, Agent, or Firm* — Cesari and McKenna, LLP (57) ABSTRACT

The present invention provides a full human anti-TNF-α monoclonal antibody, the preparation method and use thereof. The antibody in the present invention has an amino acid sequence of heavy chain variable region as shown in SEQ ID NO: 6 and an amino acid sequence of light chain variable region as shown in SEQ ID NO: 8. The antibody in the present invention can be used to prepare medicines for the treatment of autoimmune disorders.

13 Claims, 2 Drawing Sheets

Fig. 3

FULLY HUMAN ANTI-TNF-ALPHA MONOCLONAL ANTIBODY, PREPARATION METHOD AND USE THEREOF

CROSS-REFERENCE TO RELATED APPLICATIONS

This application is the National Stage of International Application No. PCT/CN2010/000512, filed on Apr. 16, 2010, which claims the priority of Chinese Application No. 201010125249.7, filed on Feb. 25, 2010. The contents of both applications are hereby incorporated by reference in their entirety.

FIELD OF THE INVENTION

The present invention relates to the field of biotechnology. In particular, the present invention relates to a fully human monoclonal antibody, the preparation method and use thereof.

BACKGROUND OF THE INVENTION

TNF-α is a multifunctional immunomodulatory molecule in vivo that can work by binding to the cytomembrane receptor, which always causes target cell death (where its name is derived from) or induces local aggregation of immune effector cells. TNF-α is a soluble homologous trimeric subunit having a molecular weight of 17 KD (Smith, et al., J. Biol. Chem. 262:6951-6954, 1987). A transmembrane binding precursor of TNF-α with a molecular weight of 26 KD has also been found (Kriegler, et al., Cell 53:45-53, 1988). Mononuclear macrophages can secrete TNF-α and TNF-β when simulated with endotoxin and other stimulus, and some other cells can also secrete TNF-α.

TNF-α plays a crucial role in the pathological process of rheumatoid arthritis, bacterial or viral infection, chronic inflammation, autoimmune diseases such as AIDS, malignant tumors and/or neurodegenerative diseases. TNF-α monoclonal antibody can neutralize TNF-α and negatively regulate the activity of TNF-α in vivo. Moreover, a large number of studies have shown that TNF-α is the main medium which may cause septic shock syndrome. The increase of TNF-α level in blood serum of patients suffering from septic shock syndrome indicates the increase of mortality rate and disability rate. The clinical use of TNF-α antibody or its receptor has a certain therapeutic effect on septic shock syndrome.

In addition, TNF-α is one of the main media for promoting asymptomatic HIV infection status into AIDS, and monoclonal antibodies against TNF-α can neutralize the activity of TNF-α, negatively regulate the activity of TNF-α in vivo, and may remove the inducement from asymptomatic infection status into AIDS and achieve a certain purpose of AIDS treatment. Combined use of a TNF-α monoclonal antibody and other AIDS drugs counteracts the side effect due to excessive TNF-α and will distinctly enhance the therapeutic effect.

Initially, the scientists prepared and obtained murine anti-TNF-α monoclonal antibodies which were used to neutralize TNF-α. However, studies have shown that murine monoclonal antibodies have many disadvantages as drugs for treatment, because when used in the human body, the murine monoclonal antibodies have strong immunogenicity and fast elimination in vivo with a short half life, leading to limited clinical efficacy and considerable side effects. With the development of humanized monoclonal antibody technology, the disadvantages of the anti-TNF-α murine monoclonal antibody have been overcome. Thereamong, a human-mouse chimeric anti-TNF-α monoclonal antibody, Infliximab (REMICADE®), has been prepared through upstream construction techniques of genetic engineering, the variable region of which is still derived from murine TNF-α monoclonal antibody, maintaining the specificity and affinity binding to soluble fragments and transmembrane domains of tumor necrosis factor (Ka=$10^{10}$ $M^{-1}$), and the constant region of which is replaced by the human IgG1 constant region, extending the in vivo half life considerably. Other TNF-α inhibitors that have been approved for marketing abroad include an antibody fusion protein (etanercept; ENBREL®, Amgen) and a fully human anti-tumor necrosis factor-α monoclonal antibody (adalimumab; HUMIRA®, Abbott).

From the standpoints of target and specificity of action, these drugs mentioned above have almost the same mechanism of action, but all the above antibodies and fusion protein have varying degrees of problems such as high immunogenicity, low specificity and deficient stability. Therefore, there is an urgent need to establish an anti-TNF-α antibody that not only can maintain or increase the affinity and specificity of the antibody but also can reduce or eliminate the antibody immunogenicity, thereby further improving the safety and efficiency in clinical application.

SUMMARY OF THE INVENTION

The present invention constructs a very large human natural phage antibody library and obtains a fully human anti-TNF-α antibody 4H16 by selecting therefrom.

More particularly, the present invention provides a fully human anti-TNF-α antibody, having an amino acid sequence of heavy chain variable region as shown in SEQ ID NO: 6, and an amino acid sequence of light chain variable region as shown in SEQ ID NO: 8.

The above fully human anti-TNF-α antibody according to the present invention has an amino acid sequence of heavy chain as shown in SEQ ID NO: 10, and an amino acid sequence of light chain as shown in SEQ ID NO: 12.

The present invention also provides an isolated nucleotide encoding the above fully human anti-TNF-α antibody.

The above nucleotide according to the present invention has a nucleotide sequence encoding heavy chain variable region of the fully human anti-TNF-α antibody as shown in SEQ ID NO: 5, and a nucleotide sequence encoding light chain variable region of the fully human anti-TNF-α antibody as shown in SEQ ID NO: 7.

The above nucleotide according to the present invention has a nucleotide sequence encoding heavy chain of the fully human anti-TNF-α antibody as shown in SEQ ID NO: 9, and a nucleotide sequence encoding light chain of the fully human anti-TNF-α antibody as shown in SEQ ID NO: 11.

The present invention also provides an expression vector containing the above nucleotide, which is pcDNA3.1/ZEO(+) or pcDNA3.1(+).

The present invention also provides a host cell transfected with the above expression vector, which is CHO-K1 cell.

The present invention further provides a method for preparing the above fully human antibody, comprising selecting human phage antibody library to obtain a fully human anti-TNF-α single-chain antibody with high affinity; constructing an eukaryotic expression vector of the complete molecular of the fully human anti-TNF-α antibody; expressing the complete molecular of fully human anti-TNF-α antibody in CHO cells; and purifying the complete molecular of the fully human anti-TNF-α antibody.

The present invention also provides a use of the above fully human anti-TNF-α antibody in preparing medicines for treatment of autoimmune diseases. The autoimmune diseases are selected from rheumatoid arthritis, ankylosing spondylitis or psoriasis.

The obtained antibodies are used to perform a series of experiments in the present invention and the experiment results show that compared to D2E7 (adalimumab monoclonal antibody, Abbott), and 7B3 disclosed in Chinese Patent Application No. 200310108440.0 entitled "Fully Human Tumor Necrosis Factor Antibody, Preparation Method and Pharmaceutical Composition Thereof" filed on Nov. 6, 2003, the antibodies obtained according to the present invention have higher antibody affinity and stronger TNF-α neutralizing capacity.

DETAILED DESCRIPTION OF THE INVENTION

The following examples and experiment examples are used to further illustrate the present invention only and should not be construed to limit the present invention.

Example 1

Preparation of Antibody (1) Cloning of Genes Encoding Human Antibody Light and Heavy Chain Constant Region Healthy human lymphoma cells were isolated with lymphocyte separation medium (Dingguo Biotechnology Development Company, CHINA), and total RNA was extracted using Trizol reagent (Invitrogen). The genes encoding antibody heavy and light chain constant region were amplified by RT-PCR reaction, with the primers designed according to the sequences reported in the reference (Cell, 1980, 22: 197-207) and reference (Nucleic Acids Research, 1982, 10: 4071-4079), respectively. The PCR products were purified by agarose gel electrophoresis and recovered and cloned into pGEM-T vectors (Promega). Correct clones were obtained by sequencing verification. SEQ ID NO: 1 and SEQ ID NO: 2 show the nucleotide sequence and amino acid sequence of the heavy chain constant region ($C_H$), respectively. SEQ ID NO: 3 and SEQ ID NO: 4 show the nucleotide sequence and amino acid sequence of the light chain constant region ($C_L$), respectively. In this example, the correct clones were designated as pGEM-T/$C_H$ and pGEM-T/$C_L$.

(2) Preparation of cDNA 20 ml of peripheral blood was collected from each of 50 healthy people and mononuclear cells were isolated with lymphocyte separation medium after mixing the collected blood (Tianjin blood research Institute of Medical Science). Total cellular RNA was extracted from the isolated human peripheral blood lymphocytes using Trizol reagent (Invitrogen). cDNA was reverse transcribed using cDNA reverse transcription kit (Shanghai Biocolor Biotechnology Ltd.). The above procedures were performed according to the manufacturer's instructions.

(3) Design of Primers $V_H$Back, $V_H$For, $V_L$Back and $V_L$For, the primers for cloning genes of human antibody heavy chain variable region ($V_H$) and light chain variable region ($V_L$), were designed and synthesized according to the reference (Immunotechnology, 1998, 3:271-278). Sequences of $V_H$Back, $V_H$For, $V_L$Back and $V_L$For were shown in Immunotechnology, 1998, 3:271-278. Wherein, $V_H$Back primer was added with an Sfi I site-containing sequence: atg gcc cag ccg gcc atg gcc (SEQ ID NO: 13) at the 5' end; $V_H$For primer was added with a sequence: gcc aga acc acc gcc gcc gga gcc acc acc gcc (SEQ ID NO: 14) at the 5' end; $V_L$Back primer was added with a sequence: tcc ggc ggc ggt ggt tct ggc gga ggc gga tct (SEQ ID NO: 15) at the 5' end; and $V_L$For primer was added with a Not I site-containing sequence: atg cgg ccg c (SEQ ID NO: 16) at the 5' end.

(4) Construction and Selection of Phage Antibody Library

Phage single-chain antibody library was constructed with the cDNA of (2) and the primers of (3) using recombinant Phage antibody system kit (Amersham Biosciences) and then selected with a specific antigen. The methods of constructing and selecting the antibody library were performed according to the instructions of recombinant phage antibody system kit. The specific antigen used for selecting "recombinant human TNF-α (rhTNF-α)" was purchased from R&D. An anti-TNF-α single-chain antibody 4H16ScFv was obtained after several times of selection, and its gene sequence was obtained by sequencing. SEQ ID NO: 5 and SEQ ID NO: 6 show the nucleotide sequence and amino acid sequence of the heavy chain variable region ($V_H$) of 4H16ScFv, respectively. SEQ ID NO: 7 and SEQ ID NO: 8 show the nucleotide sequence and amino acid sequence of the light chain variable region ($V_L$) of 4H16ScFv, respectively.

(5) Expression of Fully Human Antibody in Eukaryotic Cells

4H16ScFv genes and pGEM-T/$C_H$ vectors were used as template to synthesize fully human antibody heavy chain genes by overlapping PCR. The reaction conditions were: 95° C. for 15 min; 94° C. for 50 sec, 58° C. for 50 sec, 72° C. for 50 sec, for 30 cycles; 72° C. for 10 min. Besides, the fully human antibody heavy chain genes were allowed to contain HindIII restriction enzyme sites and a signal peptide gene sequence at the 5' end and contain translation stop codons TAA and EcoRI restriction enzyme sites at the 3' end. The sequence of the signal peptide was: (ATGGATTTTCAGGT-GCAGATTTTCAGCTTCCT GCTAATCAGTGCCT-CAGTCATAATATCCA GAGGA) (SEQ ID NO: 17). Finally, PCR amplification products were separated by agarose gel electrophoresis and the band of interest was recovered and cloned into pGEM-T vectors (Promega) to select and sequence positive clones. Clones with the correct sequence were selected and digested with Hind III and EcoRI, and the fully human antibody heavy chain fragments 4H16VHCH were purified and recovered by agarose gel electrophoresis and ligated into the HindIII and EcoRI-digested plasmids pcDNA3.1(+) (Invitrogen) to construct fully human heavy chain eukaryotic expression vectors pcDNA3.1(+) (4H16VHCH).

4H16ScFv genes and pGEM-T/$C_L$ vectors were used as template to synthesize fully human antibody light chain genes by overlapping PCR. The reaction conditions were: 95° C. for 15 min; 94° C. for 50 sec, 58° C. for 50 sec, 72° C. for 50 sec, for 30 cycles; 72° C. for 10 min. The obtained PCR products contained HindIII restriction enzyme sites and a signal peptide gene sequence at the 5' end and contained translation stop codons TAA and EcoRI restriction enzyme sites at the 3' end. The sequence of the signal peptide was: (ATG GATTTTCAGGTGCAGATTT TCAGCTTCCTGCTAAT- CAGTGCCTCAGTCATAATATCCAGAGGA) (SEQ ID NO: 17). Clones with the correct sequences were selected and digested with Hind III and EcoRI, and the fully human antibody light chain fragments 4H16$V_LC_L$ were purified and recovered by agarose gel electrophoresis and ligated into the HindIII and EcoRI-digested plasmids pcDNA3.1/ZEO(+) (Invitrogen) to construct fully human light chain eukaryotic expression vectors pcDNA3.1/ZEO(+) (4H16$V_LC_L$).

3×10$^5$ CHO-K1 cells (ATCC CRL-9618) were inoculated into 3.5 cm tissue culture dishes, and transfected when the cells were cultured to 90-95% confluence: 10 μg of plasmids (4 μg of plasmids pcDNA3.1(+) (4H16$V_HC_H$), 6 μg of plasmids pcDNA3.1/ZEO(+) (4H16$V_LC_L$)) and 20 μl of Lipofectamine2000 Reagent (Invitrogen) were taken to perform transfection according to the instructions of Lipofectamine2000 Reagent kit. After transfection for 24 hours, the cells were transferred to DMEM medium containing 600 μg/ml G418 (Invitrogen) and 250 μg/ml Zeocin (Invitrogen) to select resistant clones. Cell culture supernatants were taken to select high-expressing clones by ELISA: ELISA plates were coated with goat anti-human IgG (Fc) overnight at 4° C. and blocked with 2% BSA-PBS at 37° C. for 2 h; the culture supernatants of resistant clones to be tested or standard sample (Human myeloma IgG1, κ) (Sigma) were added and warm incubated at 37° C. for 2 h; HRP-goat anti-human IgG (κ) (Southern Biotechnology Associates) was added and warm incubated at 37° C. for 1 h for combining reaction, and chromogenic reagent TMB was added and reacted at 37° C. for 5 min, finally $H_2SO_4$ was used to stop the reaction and $A_{450}$ value was measured. The high-expressing clones obtained by selection were enlarged cultured in serum-free medium, and fully human antibodies 4H16 were isolated and purified by Protein A affinity column (GE). The purified antibodies were dialyzed against PBS and finally quantified by UV absorbance. SEQ ID NO: 9 and SEQ ID NO: 10 show the nucleotide sequence and amino acid sequence of the heavy chain of fully human antibody 4H16, respectively. SEQ ID NO: 11 and SEQ ID NO: 12 show the nucleotide sequence and amino acid sequence of the light chain of fully human antibody 4H16, respectively.

EXPERIMENTAL EXAMPLES

7B3 was prepared according to the method described in Chinese Patent Application No. 200310108440.0 entitled "Fully Human Tumor Necrosis Factor Antibody, Preparation Method and Pharmaceutical Composition Thereof" filed on Nov. 6, 2003.

Experimental Example 1

Affinity Detection of Anti-TNF-α Antibody

Affinity constant of TNFα antibody was detected by plasmon resonance of the surface Plasmon (SPR) using Biacore T100 system (Biacore AB, Uppsala, Sweden). Recombinant TNFα (R&D) was covalently linked to CM5 biological sensor chips (Biacore) by amino-coupling. (1) fully human antibody 4H16; (2) fully human antibody adalimumab (HUMIRA®, D2E7, commercial product); (3) fully human anti-TNFα antibody 7B3 as positive control; and (4) antibody Trastuzumab as negative control were formulated with PBS/ 0.05% TWEEN-20 (ICI Americas) (an eradicator) into solutions with different concentrations (2-fold dilution) and passed through the chips at a flow rate of 50 μl/min. After each examination, they were washed with 5 μl of 50 mM hydrochloric acid aqueous solution at a flow rate of 3 μl/min so as to wash away the residual antibodies from the immobilized ligands. The binding curves were subjected to nonlinear regression analysis using BIAevalution software (T100 evalution version 2.0, Biacore). The results are shown in table 1. The KD value of fully human antibody 4H16 was significantly lower than that of fully human antibody adalimumab and fully human TNFα antibody 7B3, demonstrating that the affinity of fully human antibody 4H16 to TNFα was higher than that of adalimumab and fully human TNF-α antibody 7B3. The experimental results are shown in Table 1.

TABLE 1

| Experiment results of affinity | | | |
|---|---|---|---|
| Antibody | Kon (M−1S−1/10$^5$) | Koff (10$^5$S−1) | KD (nM) |
| 4H16 | 1.58 | 5.7 | 0.36 |
| adalimumab | 1.35 | 8.5 | 0.63 |
| 7B3 | 1.32 | 9.5 | 0.72 |
| Trastuzumab | ND | ND | ND |

Experimental Example 2

Experiment of Blocking the Binding of TNF-α to Soluble P75 by Anti-TNF-α Antibody 4H16

Figure 1:
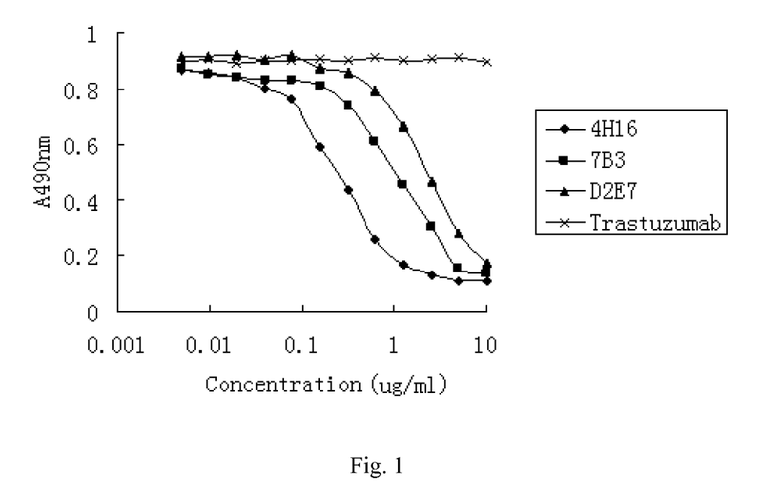
FIG. 1 shows the experiment results of blocking the binding of TNF-α to soluble P75 receptor by anti-TNF-α antibody 4H16.

10 μg/ml of P75 receptor-Fc fusion protein (which was prepared according to the method described in Chinese Patent Application No. 01132074.5 entitled "Recombinant genes, fusion genes and products of the soluble fragment of Tumor Necrosis Factor Receptor" filed on Oct. 31, 2001) was used to coat ELISA plates and reacted at 37° C. for 2 h; 3% BSA-PBS was used to block the plate wells and reacted overnight at 4° C. Biotin-labeled TNF-α (Product 210-TA-050 of R&D, obtained using EZ-Link Sulfo-NHS-Biotinylation Kit 21425 of Pierce) was diluted into 10 ng/ml with PBS. Fully human monoclonal antibody 4H16 (the antibody of the present invention), D2E7 (adalimumab monoclonal antibody, Abbott), 7B3 and negative control antibody Trastuzumab (Genentech) were diluted into 10 μg/ml using the above diluted solution and subjected to serial 2-fold dilution. The diluted samples and control samples were added to washed ELISA plates with 100 μl/well and reacted at 37° C. for 1 h; the ELISA plates were washed; HRP-avidin (Zymed) was diluted at 1:1000 with PBS and added to the ELISA plates with 100 μl/well and reacted at 37° C. for 1 h; the ELISA plates were washed; equal volumes of A solution and B solution (Jingmei BioTech Co. Ltd.) of TMB substrate for HRP were mixed and added to the ELISA plates with 100 μl/well and reacted at room temperature for 10 minutes in darkness; each well was added with 100 μl of 0.5M sulphuric acid to stop the reaction. Absorbance at 490 nm was measured using microplate reader. The concentration of samples was used as x-coordinate and absorbance was used as y-coordinate. The results are shown in Table 2 and FIG. 1.

TABLE 2

| No. | IC50 (μg/ml) | | |
|---|---|---|---|
| | 4H16 | 7B3 | D2E7 |
| 1 | 0.25 | 1.19 | 2.30 |
| 2 | 0.31 | 1.42 | 2.15 |
| 3 | 0.27 | 1.06 | 2.59 |
| Average | 0.28 ± 0.03 | 1.22 ± 0.18 | 2.35 ± 0.22 |

The experiment results showed that fully human anti-TNF-α monoclonal antibody 4H16 of the present invention blocked the binding of TNF-α to P75 receptor with the smallest IC50, thus it had the highest affinity to TNF-α.

Experimental Example 3

Experiment of Blocking the Binding of TNF-α to U-937 Cell Surface Receptor by Anti-TNF-α Antibody 4H16

Figure 2:
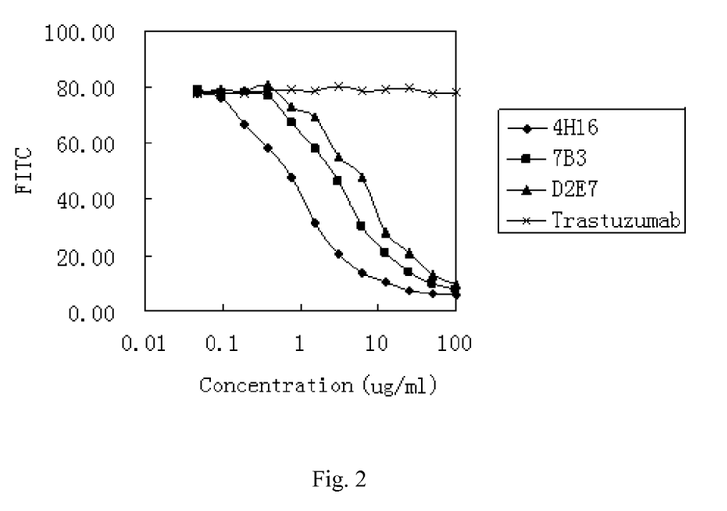
FIG. 2 shows the experiment results of blocking the binding of TNF-α to U-937 cell surface receptor by anti-TNF-α antibody 4H16.

U937 cells (ATCC CRL1593) were cultured in RPMI-1640 medium (GIBCO) containing 10% fetal bovine serum (JRH). TNF-α receptors were expressed on the surface of the cells. The cells at logarithmic growth phase were counted and then centrifuged at 200 g for 5 min. Supernatant was removed and cell pellets were resuspended in PBS containing 1% fetal bovine serum. The cells were adjusted to a concentration $1 \times 10^6$/ml, and then distributed into flow cytometry test tubes, with 100 μl/tube. Fluorescein isothiocyanate (FITC, Amresco)-labelled TNF-α (Product 210-TA-050, R&D) was diluted into 100 ng/ml using PBS. Fully human anti-TNF-α monoclonal antibody 4H16 (the antibody of the present invention), D2E7 (adalimumab monoclonal antibody, Abbott), 7B3 and negative control antibody Trastuzumab (Genentech) were diluted into 100 μg/ml using the above diluted solution, and subjected to serial 2-fold dilution. The diluted samples and control samples were added into flow cytometry test tubes, with 100 μl/tube, and reacted at 4° C. for 1 hour in darkness; the cells were washed twice with PBS containing 1% fetal bovine serum, and centrifuged at 200 g for 5 min each time. Supernatant was removed and cell pellets were resuspended in 300 μl of PBS containing 1% fetal bovine serum. Flow cytometry was used to measure the fluorescence intensity of each tube. Sample concentration was plotted on the x-coordinate and absorbance was plotted on the y-coordinate. The results were shown in Table 3 and FIG. 2.

TABLE 3

| Experiment No. | IC50 (μg/ml) | | |
|---|---|---|---|
| | 4H16 | 7B3 | D2E7 |
| 1 | 0.89 | 3.42 | 6.62 |
| 2 | 1.03 | 3.06 | 8.03 |
| 3 | 0.97 | 4.15 | 7.44 |
| Average | 0.96 ± 0.07 | 3.54 ± 0.56 | 7.36 ± 0.71 |

The experiment results showed that fully human anti-TNF-α monoclonal antibody 4H16 of the present invention blocked the binding of TNF-α to U937 cell surface receptors with the smallest IC50, thus it had the highest affinity to TNF-α

Experimental Example 4

Resistance to TNF-α-Mediated Killing of L929 Cells by Anti-TNF-α Antibody

Figure 3:
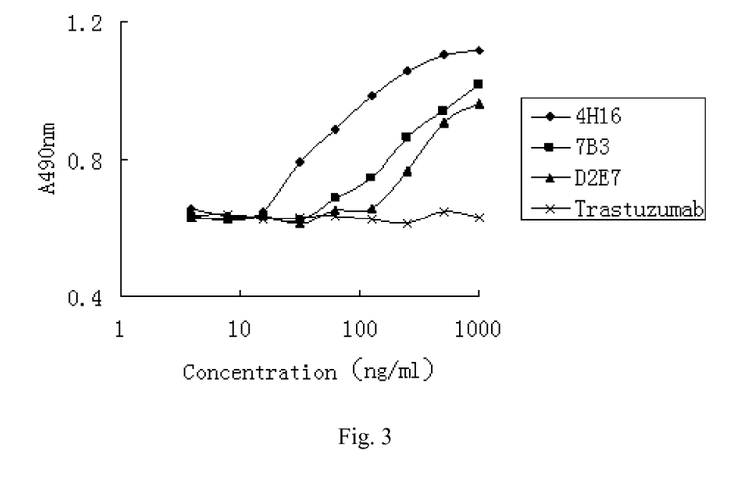
FIG. 3 shows the experiment results of the resistance to TNF-α-mediated killing in L929 cells by anti-TNF-α antibody 4H16.

L929 cells (ATCC CCL-1) were cultured in RPMI-1640 medium (GIBCO) containing 10% fetal bovine serum (JRH). The cells were digested and counted in logarithmic growth phase and then centrifuged at 200 g for 5 min. Supernatant was removed and cell pellets were resuspended in the above medium. The cells were adjusted to a concentration $1 \times 10^5$/ml, then added in a 96-well culture plate with 100 μl/well and cultured overnight in a 5% $CO_2$ incubator at 37° C. Next day, the culture solution was added with actinomycin D (Huamei Biotechnology Co., Ltd) until reaching a concentration of 20 μg/ml and TNF-α (Product 210-TA-050, R&D) until reaching a concentration of 4 ng/ml. Fully human anti-TNF-α monoclonal antibody 4H16 (the antibody of the present invention), D2E7 (adalimumab monoclonal antibody, Abbott), 7B3 and negative control antibody Trastuzumab (Genentech) were diluted into 1 μg/ml using the medium containing actinomycin D and TNF-α, and subjected to serial 2-fold dilution. The diluted samples and control samples were added in a 96-well culture plate that was incubated with L929 cells at 100 μl/well, and duplicate wells were set. They were cultured in a 5% $CO_2$ incubator at 37° C. for 20 hours. Freshly prepared non-radioactive cell proliferation detection reagent (Promega), namely a mixture of MTS and PMS in a ratio of 20:1, was added to a 96-well culture plate at 20 μl/well and cultured for another 3 hours in the incubator. Absorbance at 490 nm was measured using microplate reader, with 630 nm as reference wavelength. Sample concentration was plotted on the x-coordinate and absorbance was plotted on the y-coordinate. The results are shown in Table 4 and FIG. 3.

TABLE 4

| Experiment No. | IC50 (ng/ml) | | |
|---|---|---|---|
| | 4H16 | 7B3 | D2E7 |
| 1 | 59.2 | 224.3 | 296.3 |
| 2 | 45.9 | 247.1 | 335.2 |
| 3 | 66.4 | 210.2 | 317.8 |
| Average | 57.17 ± 10.40 | 227.20 ± 18.62 | 316.43 ± 19.49 |

The experiment results showed that fully human anti-TNF-α monoclonal antibody 4H16 of the present invention resisted the TNF-α-mediated killing effect in L929 cells with the smallest IC50, thus it had the highest affinity to TNF-α and the strongest ability to neutralize TNF-α.

Experimental Example 5

Resistance to TNF-α-Induced Death in Mice by Anti-TNF-α Antibody

The injection of recombinant human TNF-α may induce death in D-galactosamine-sensitized mice. Intraperitoneal injection of 1 μg of recombinant human TNF-α (Product 210-TA-050, R&D) and 20 mg of D-galactosamine (Amresco) may induce death in 80-90% of C57BL6 mice (Vital River Lab Animal Technology Inc., Beijing, China). In this experiment, first a certain amount of each antibody was administrated by intraperitoneal injection; after 30 minutes, 1 μg of recombinant human TNF-α and 20 mg of D-galactosamine were intraperitoneally injected. The preventive effect of each antibody was observed. The injection dosage and result of each group are shown below in table 5.

TABLE 5

Survival Status of Mice

| Injection Dosage | 4H16 | 7B3 | D2E7 | Trastuzumab |
|---|---|---|---|---|
| 10 μg | 10/10 (100%) | 8/10 (80%) | 7/10 (70%) | 0/10 (0%) |
| 8 μg | 10/10 (100%) | 7/10 (70%) | 6/10 (60%) | 0/10 (0%) |
| 6 μg | 9/10 (90%) | 7/10 (70%) | 5/10 (50%) | 1/10 (10%) |
| 4 μg | 8/10 (80%) | 6/10 (60%) | 4/10 (40%) | 0/10 (0%) |
| 2 μg | 8/10 (80%) | 5/10 (50%) | 4/10 (40%) | 1/10 (10%) |
| 1 μg | 7/10 (70%) | 5/10 (50%) | 2/10 (20%) | 0/10 (0%) |
| 0 | 0/10 (0%) | 1/10 (10%) | 1/10 (10%) | 0/10 (0%) |
| 10 μg (without TNF-α) | 10/10 (100%) | 10/10 (100%) | 10/10 (100%) | 10/10 (100%) |

The above experiment results showed that fully human anti-TNF-α monoclonal antibody 4H16 had the greatest efficiency on resisting TNF-α-induced death in mice, thus the antibody had the most excellent ability to neutralize mouse TNF-α in vivo.

Experimental Example 6

Inhibition of TNF-α-Induced Fevering in Rabbit by Anti-TNF-α Antibody 4H16

New Zealand white rabbits were intravenously injected with recombinant human TNF-α to induce febrile reaction. 5 μg/kg of recombinant human TNF-α may induce a febrile reaction of about 0.5° C. in rabbits. In this experiment, New Zealand white rabbits were intravenously injected with a mixture of recombinant human TNF-α at 5 μg/kg body weight and each antibody at different dosages. Body temperatures of the tested animals were monitored before injection and at 60 minutes after injection to evaluate the ability of each antibody to neutralize the biological effect of recombinant human TNF-α. The injection dosage and result of each group are shown below in table 6.

TABLE 6

Increase in Body Temperature of Rabbits

| Injection Dosage | 4H16 | 7B3 | D2E7 | Trastuzumab |
|---|---|---|---|---|
| 500 μg/kg | 0° C. | 0° C. | 0° C. | 0.5° C. |
| 100 μg/kg | 0° C. | 0° C. | 0.2° C. | 0.6° C. |
| 20 μg/kg | 0° C. | 0.3° C. | 0.3° C. | 0.5° C. |
| 4 μg/kg | 0.2° C. | 0.4° C. | 0.4° C. | 0.5° C. |
| 0 | 0.5° C. | 0.4° C. | 0.4° C. | 0.5° C. |
| 500 μg/kg (without TNF-α) | 0° C. | 0° C. | 0° C. | 0° C. |

The above experiment results showed that fully human anti-TNF-α monoclonal antibody 4H16 of the present invention had the best effect on inhibiting TNF-α induced fevering of rabbit, thus the antibody had the most excellent ability of neutralizing rabbit TNF-α in vivo.

What is claimed is:

1. A fully human anti-TNF-α monoclonal antibody, having an amino acid sequence of heavy chain variable region as shown in SEQ ID NO: 6 and an amino acid sequence of light chain variable region as shown in SEQ ID NO: 8.

2. The fully human anti-TNF-α monoclonal antibody of claim 1, having an amino acid sequence of heavy chain as shown in SEQ ID NO: 10 and an amino acid sequence of light chain as shown in SEQ ID NO: 12.

3. A nucleic acid encoding the fully human anti-TNF-α antibody of claim 1, having a nucleotide sequence of heavy chain variable region as shown in SEQ ID NO: 5 and a nucleotide sequence of light chain variable region as shown in SEQ ID NO: 7.

4. The nucleic acid of claim 3, having a nucleotide sequence of heavy chain as shown in SEQ ID NO: 9 and a nucleotide sequence of light chain as shown in SEQ ID NO: 11.

5. An expression vector containing the nucleic acid of claim 3, wherein the expression vector is pcDNA3.1/ZEO(+) or pcDNA3.1(+).

6. A host cell containing the expression vector of claim 5, wherein the host cell is a CHO-K1 cell.

7. A method of preparing the fully human anti-TNF-α monoclonal antibody of claim 1, comprising the steps of: selecting human phage antibody library to obtain a fully human anti-TNF-α single-chain antibody with high affinity; constructing a eukaryotic expression vector of the complete molecule of the fully human anti-TNF-α antibody; expressing the complete molecule of the fully human anti-TNF-α antibody in CHO cells; and purifying the complete molecule of the fully human anti-TNF-α antibody.

8. A method for treating an autoimmune disease, comprising administering to a subject in need thereof the fully human anti-TNF-α monoclonal antibody of claim 1.

9. The method of claim 8, wherein said autoimmune disease is rheumatoid arthritis, ankylosing spondylitis, or psoriasis.

10. An expression vector containing the nucleic acid of claim 4, wherein the expression vector is pcDNA3.1/ZEO(+) or pcDNA3.1(+).

11. A host cell containing the expression vector of claim 10, wherein the host cell is a CHO-K1 cell.

12. A method for treating an autoimmune disease, comprising administering to a subject in need thereof the fully human anti-TNF-α monoclonal antibody of claim 2.

13. The method of claim 12, wherein said autoimmune disease is rheumatoid arthritis, ankylosing spondylitis, or psoriasis.

* * * * *

SEQUENCE LISTING

```
<160> NUMBER OF SEQ ID NOS: 17

<210> SEQ ID NO 1
<211> LENGTH: 990
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of human antibody heavy
      chain constant region (CH)

<400> SEQUENCE: 1
gctagcacca  agggcccatc  ggtcttcccc  ctggcaccct  cctccaagag  cacctctggg     60
ggcacagcgg  ccctgggctg  cctggtcaag  gactacttcc  ccgaaccggt  gacggtgtcg    120
tggaactcag  gcgccctgac  cagcggcgtg  cacaccttcc  cggctgtcct  acagtcctca    180
ggactctact  ccctcagcag  cgtggtgacc  gtgccctcca  gcagcttggg  cacccagacc    240
tacatctgca  acgtgaatca  caagcccagc  aacaccaagg  tggacaagaa  agttgagccc    300
aaatcttgtg  acaaaactca  cacatgccca  ccgtgcccag  cacctgaact  cctgggggga    360
ccgtcagtct  tcctcttccc  cccaaaaccc  aaggacaccc  tcatgatctc  ccggacccct    420
gaggtcacat  gcgtggtggt  ggacgtgagc  cacgaagacc  ctgaggtcaa  gttcaactgg    480
tacgtggacg  gcgtggaggt  gcataatgcc  aagacaaagc  cgcgggaaga  gcagtacaac    540
```

```
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900 cagcaggga acgtcttctc atgctccgtg atgcatgagg ctctgcacaa ccactacacg    960
cagaagagcc tctccctgtc tcccggtaaa                                     990
```

```
<210> SEQ ID NO 2
<211> LENGTH: 330
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of human antibody heavy
      chain constant region (CH)

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 318
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of human antibody light
      chain constant region (CL)

<400> SEQUENCE: 3
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgt                                                   318

<210> SEQ ID NO 4
<211> LENGTH: 106
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of human antibody light
      chain constant region (CL)

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 5
<211> LENGTH: 378
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: misc_feature
<223> OTHER INFORMATION: Nucleotide sequence of heavy chain variable
      region of fully human antibody 4H16

<400> SEQUENCE: 5

```
caggtcacct tgagggagtc tggtcctgcg ctggtgaaac ccacacagac cctcacactg    60
acctgcacct tctctgggtt ctcactcagc actagtggaa tgtgtgtgag ctggatccgt   120
cagcccccag ggaaggccct ggagtggctt gcactcattg attgggatga tgataaatac   180
tacagcacat ctctgaagac caggctcacc atctccaagg acacctccaa aaaccaggtg   240
gtccttacaa tgaccaacat ggaccctgtg acacagcca cgtattactg tgcacggata   300
cttgtggata tagtggctac gattacaaat gatgcttttg atgtctgggg ccaagggaca   360
atggtcaccg tctcttca                                                 378
```

<210> SEQ ID NO 6
<211> LENGTH: 126
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of heavy chain variable
      region of fully human antibody 4H16

<400> SEQUENCE: 6

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Leu Val Asp Ile Val Ala Thr Ile Thr Asn Asp Ala
            100                 105                 110

Phe Asp Val Trp Gly Gln Gly Thr Met Val Thr Val Ser Ser
        115                 120                 125
```

<210> SEQ ID NO 7
<211> LENGTH: 330
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of light chain variable
      region of fully human antibody 4H16

<400> SEQUENCE: 7

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
```

-continued

| aggttcagtg gaagtggatc tgggacagat tttactttca ccatcagcag cctgcagcct | 240 |
| gaagatattg caacatatta ctgtcaacag tatgataatc tccctccaga gctcactttc | 300 |
| ggcggaggga ccaaggtgga gatcaaacgt | 330 |

<210> SEQ ID NO 8
<211> LENGTH: 110
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of light chain variable
      region of fully human antibody 4H16

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Glu Leu Thr Phe Gly Gly Gly Thr Lys Val Glu Ile Lys Arg
            100                 105                 110

<210> SEQ ID NO 9
<211> LENGTH: 1368
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of heavy chain of fully
      human antibody 4H16

<400> SEQUENCE: 9

| caggtcacct tgagggagtc tggtcctgcg ctggtgaaac ccacacagac cctcacactg | 60 |
| acctgcacct tctctgggtt ctcactcagc actagtggaa tgtgtgtgag ctggatccgt | 120 |
| cagcccccag ggaaggccct ggagtggctt gcactcattg attgggatga tgataaatac | 180 |
| tacagcacat ctctgaagac caggctcacc atctccaagg acacctccaa aaaccaggtg | 240 |
| gtccttacaa tgaccaacat ggaccctgtg gacacagcca cgtattactg tgcacggata | 300 |
| cttgtggata tagtggctac gattacaaat gatgcttttg atgtctgggg ccaagggaca | 360 |
| atggtcaccg tctcttcagc tagcaccaag ggcccatcgg tcttccccct ggcaccctcc | 420 |
| tccaagagca cctctggggg cacagcggcc ctgggctgcc tggtcaagga ctacttcccc | 480 |
| gaaccggtga cggtgtcgtg gaactcaggc gccctgacca gcggcgtgca ccttcccg | 540 |
| gctgtcctac agtcctcagg actctactcc ctcagcagcg tggtgaccgt gcctccagc | 600 |
| agcttgggca cccagaccta catctgcaac gtgaatcaca agcccagcaa caccaaggtg | 660 |
| gacaagagag ttgagcccaa atcttgtgac aaaactcaca catgcccacc gtgcccagca | 720 |
| cctgaactcc tggggggacc gtcagtcttc ctcttccccc caaaacccaa ggacaccctc | 780 |

```
atgatctccc ggacccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggaggagat gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctatag caagctcacc    1260
gtggacaaga gcaggtggca gcaggggaac gtcttctcat gctccgtgat gcatgaggct    1320
ctgcacaacc actacacgca gaagagcctc tccctgtccc cgggtaaa                 1368
```

<210> SEQ ID NO 10
<211> LENGTH: 456
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of heavy chain of fully
      human antibody 4H16

<400> SEQUENCE: 10

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Leu Val Asp Ile Val Ala Thr Ile Thr Asn Asp Ala
            100                 105                 110

Phe Asp Val Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240
```

```
Pro Glu Leu Leu Gly Gly Pro Ser Val Phe Leu Phe Pro Lys Pro
            245                 250                 255
Lys Asp Thr Leu Met Ile Ser Arg Thr Pro Glu Val Thr Cys Val Val
        260                 265                 270
Val Asp Val Ser His Glu Asp Pro Glu Val Lys Phe Asn Trp Tyr Val
    275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Glu Glu Met Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
Ser Leu Ser Leu Ser Pro Gly Lys
    450                 455
```

```
<210> SEQ ID NO 11
<211> LENGTH: 648
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<223> OTHER INFORMATION: Nucleotide sequence of light chain of fully
      human antibody 4H16

<400> SEQUENCE: 11
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcagcag cctgcagcct     240
gaagatattg caacatatta ctgtcaacag tatgataatc tccctccaga gctcactttc     300
ggcggaggga ccaaggtgga gatcaaacgt actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgcctccaa tcgggtaac      480 tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                  648

<210> SEQ ID NO 12
```

```
<211> LENGTH: 216
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Amino acid sequence of light chain of fully
      human antibody 4H16

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Glu Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
atggcccagc cggccatggc c                                             21

<210> SEQ ID NO 14
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 14
gccagaacca ccgccgccgg agccaccacc gcc                                33

<210> SEQ ID NO 15
```

```
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 15
tccggcggcg gtggttctgg cggaggcgga tct                               33

<210> SEQ ID NO 16
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 16
atgcggccgc                                                         10

<210> SEQ ID NO 17
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 17
atggattttc aggtgcagat tttcagcttc ctgctaatca gtgcctcagt cataatatcc   60
agagga                                                             66
```